United States Patent [19]

McNeil et al.

[11] Patent Number: 5,241,369
[45] Date of Patent: Aug. 31, 1993

[54] TWO-DIMENSIONAL OPTICAL SCATTEROMETER APPARATUS AND PROCESS

[76] Inventors: John R. McNeil, 13423 Desert Hills N.E., Albuquerque, N. Mex. 87113; Scott R. Wilson, 1630 Grand Ave., N.E., Albuquerque, N. Mex. 87106

[21] Appl. No.: 591,452

[22] Filed: Oct. 1, 1990

[51] Int. Cl.[5] ............................................ G01N 21/47
[52] U.S. Cl. ........................................ 356/445; 356/446
[58] Field of Search ............... 356/371, 445, 446, 340, 356/343; 358/106, 107

[56] References Cited

U.S. PATENT DOCUMENTS

| | | | |
|---|---|---|---|
| 2,803,161 | 8/1957 | Summerhayes | 356/446 |
| 3,424,912 | 1/1969 | Sargent | 356/446 |
| 4,547,073 | 10/1985 | Kugimiya | 356/371 |
| 4,555,635 | 1/1985 | Yoshida | 356/445 |

Primary Examiner—Vincent P. McGraw
Assistant Examiner—K. P. Hantis
Attorney, Agent, or Firm—William E. Hein

[57] ABSTRACT

An optical scatterometer system includes a screen positioned to receive and display a pattern representative of light specularly reflected and scattered from an illuminated sample material and a camera positioned to record the pattern displayed on the screen. The screen may present a curved surface to increase its light gathering capabilities and may be constructed of an electron trapping material, a photochromic material or a pyrochromic material. The screen may contain one or more apertures for passing one or more incident light beams generated by a light source and/or light specularly reflected and scattered from the sample material. The screen may be positioned between the sample material and the light source, or the sample material may be positioned between the screen and the light source.

30 Claims, 15 Drawing Sheets

TWO-DIMENSIONAL OPTICAL SCATTEROMETER APPARATUS AND PROCESS

REFERENCE TO RELATED APPLICATION AND PATENT

This application is related to U.S. patent Ser. No. 4,710,642 entitled Optical Scatterometer having Improved Sensitivity and Bandwidth and issued on Dec. 1, 1987, to John R. McNeil, the subject matter of which is incorporated herein by reference.

BACKGROUND AND SUMMARY OF THE INVENTION

This invention relates generally to the measurement of light scattered from a surface or volume and the use of the angular intensity spectrum of this scattered light for characterization of the microstructure of the surface or volume. More specifically, this invention measures the intensity of light using two-dimensional detectors or detector arrays. As used herein, the term microstructure refers to the morphology of the sample and the manner in which the morphology is distributed at different spatial frequencies or spatial wavelengths (i.e. structure of different lateral extent). Microstructure refers to surface as well as volume morphology of the sample.

Scattered light can be analyzed via well known models to provide a statistical analysis of the microstructure of a surface or volume sample from which the scattered light originates. This provides a simple, noncontact, and nonperturbing monitoring technique which is useful in many areas of technology to determine surface and subsurface morphology. In addition, the type and density of material defects which have simple geometric shape can be characterized using this technique. This technique is useful in such areas as microelectronics material fabrication, optoelectronics material fabrication, optical component examination, and computer disk manufacturing. Light scatter measurements are also useful for quality monitoring of fluids. For example, blood samples can be conveniently examined using light scatter techniques to reveal cell characteristics. Other fluids with particulates or small specimens held in suspension, such as oils, biological specimens, wine, gas containing particulates, and the like can be conveniently examined using light scatter measurements. Moreover, these measurements can be made in-situ to control processes used in the manufacture of the various materials described above.

A commonly used scatterometer system employs a laser light beam incident on a point of a sample and a single light detector that is mechanically rotated or scanned in an arc contained in the plane of incidence, defined by the incident and specularly reflected light beams that are centered about the point on the sample. The intensity of light scattered by the sample is measured sequentially at selected scatter angles, relative to the normal of the sample. The pattern of the scattered light intensity is then analyzed to obtain characteristics of the microstructure of the sample. Similarly, an array of detectors can be located in an arc or line segment, contained in the plane of incidence, to measure scattered light. This configuration yields the same information as the single-detector configuration, but it does so in a more efficient manner by performing a number of measurements simultaneously, rather than sequentially. Other detector configurations are known in which one detector array measures the scattered light intensity pattern in an arc or line segment located in the plane of incidence, and another detector array measures the scattered light intensity pattern in an arc or line segment located in the plane perpendicular to the plane of incidence containing the scatter point of the sample.

A shortcoming of prior art scatterometer systems is the difficulty associated with characterization of the light scattered from the sample which lies out of the plane of incidence, defined by the incident and specularly reflected laser beams. It is often desirable to characterize all of the light scattered from a sample, thereby obtaining a two-dimensional map of the scattered light intensity pattern. This is especially the case for samples which have nonisotropic microstructure and therefore scatter light nonisotropically. Examples of samples having nonisotropic microstructure include, but are not limited to, machined surfaces, single and polycrystalline materials, crystalline materials with well known defects of specific geometric shapes, microelectronic integrated circuits, electro-optic and ferroelectric materials, fluids, and fluids with materials dissolved or held in suspension. To fully characterize scattered light from a sample using prior art systems to thereby obtain a two-dimensional map of the scattered light intensity, the sample must be incrementally rotated about an axis perpendicular to the sample and passing through the point which is illuminated. After each incremental rotation, the scattered light intensity pattern is measured along an arc length. Thus, many measurements must be made sequentially to fully characterize the scattered light, resulting in a tedious and time consuming process. Alternatively, the detector may be configured such that it is capable of rotating in an arc that is out of the plane of incidence. However, this configuration adds greatly to the cost and complexity of the scatterometer system.

Known two-dimensional detector arrays have been used in conjunction with other optical elements such as lenses and apertures forming a camera. Other scatterometer systems employ only a camera as a detector element. In this arrangement, light which is scattered near the specularly reflected beam, known as the near-angle scattered light, is characterized. Similarly, the camera might be located so as to be significantly removed from the incident and specularly reflected laser beams. In this configuration, a portion of the large-angle scattered light from the sample is characterized. These configurations are significantly limited in the amount of scattered light that they characterize compared to the total amount of light scattered from the sample due to their small angular field of view.

It is therefore a principal object of the present invention to provide an improved detector system for optical scatterometers in which light specularly reflected and scattered from a sample is used to obtain a two-dimensional intensity distribution and thereby characterize the morphology of the sample in two dimensions of spatial frequency.

This and other objects are accomplished in accordance with the illustrated preferred embodiments of the present invention by employing a screen positioned to receive and display a pattern representative of light specularly reflected and scattered from an illuminated sample material and a camera positioned to record the pattern displayed on the screen. The screen may present a curved surface to increase its light gathering capabilities and may be constructed of an electron trapping material, a photochromic material or a pyrochromic material. The screen may contain one or more apertures for passing one or more incident light beams generated by a light source and/or light specularly reflected and scattered from the sample material. The screen may be positioned between the sample material and the light source, or the sample material may be positioned between the screen and the light source.

DETAILED DESCRIPTION OF THE INVENTION

Figure 1:
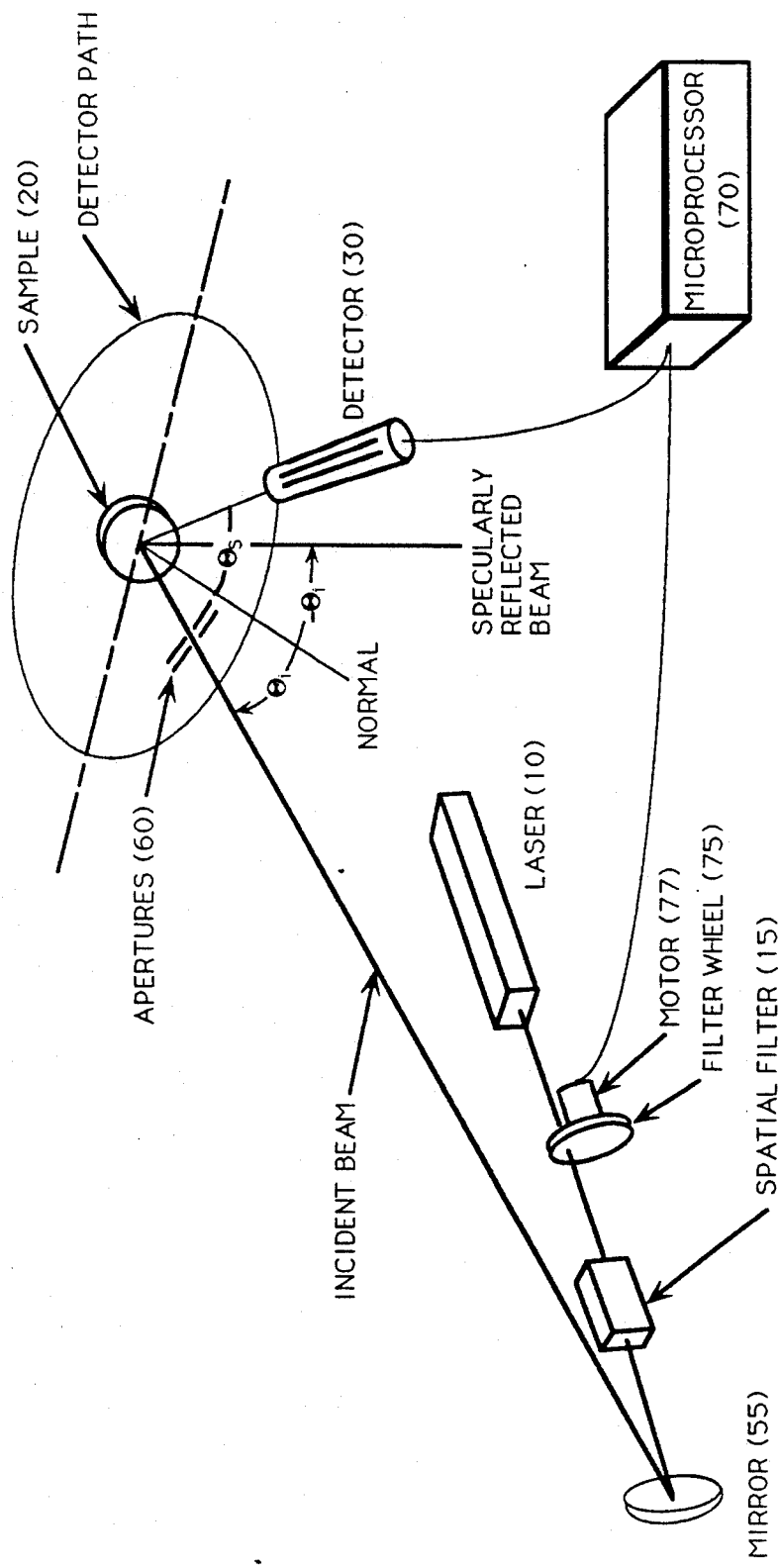
FIG. 1 is a pictorial diagram illustrating a prior art scatterometer system employing a single detector.
Figure 2:
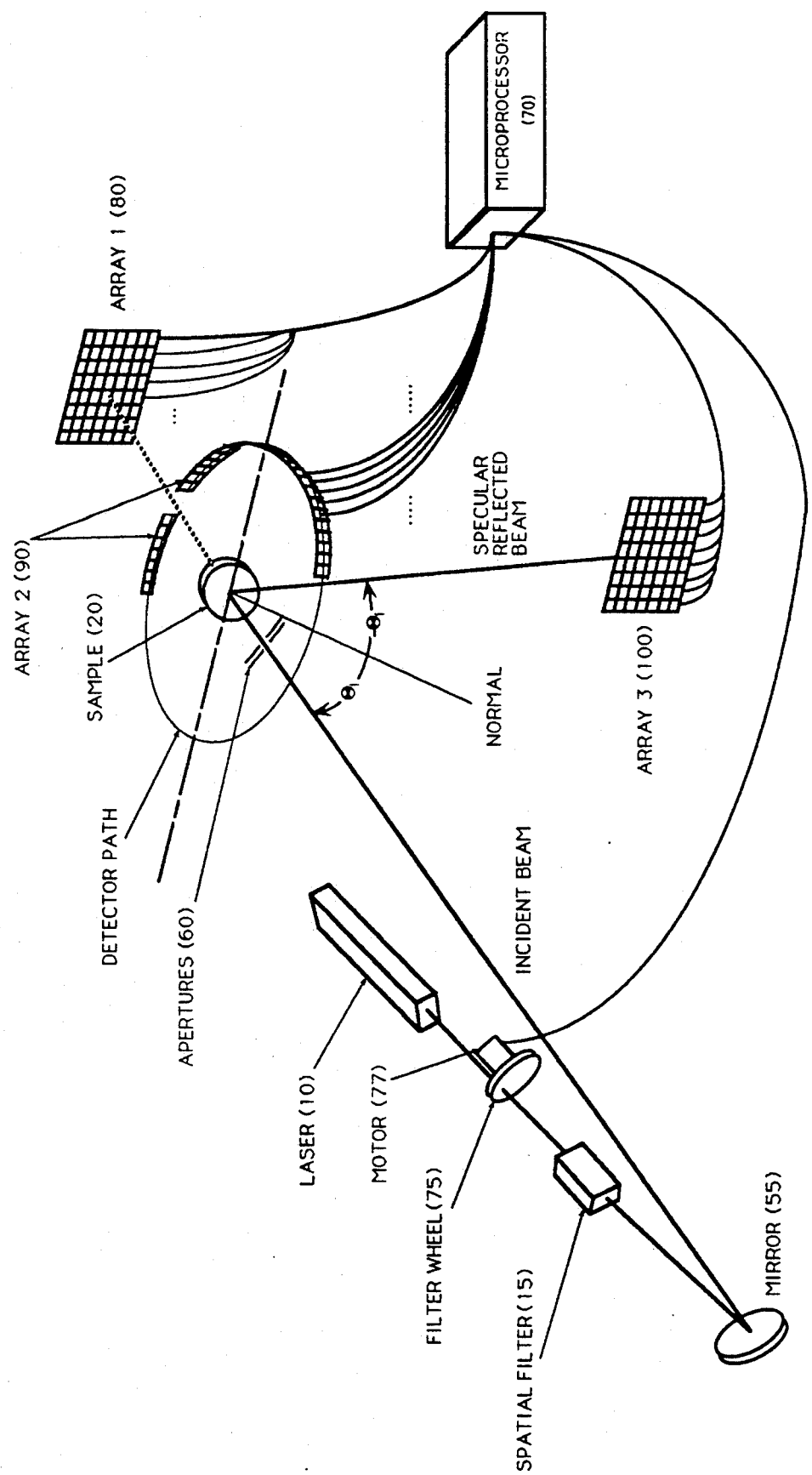
FIG. 2 is a pictorial diagram illustrating a prior art scatterometer system employing linear and two-dimensional detector arrays.
Figure 3:
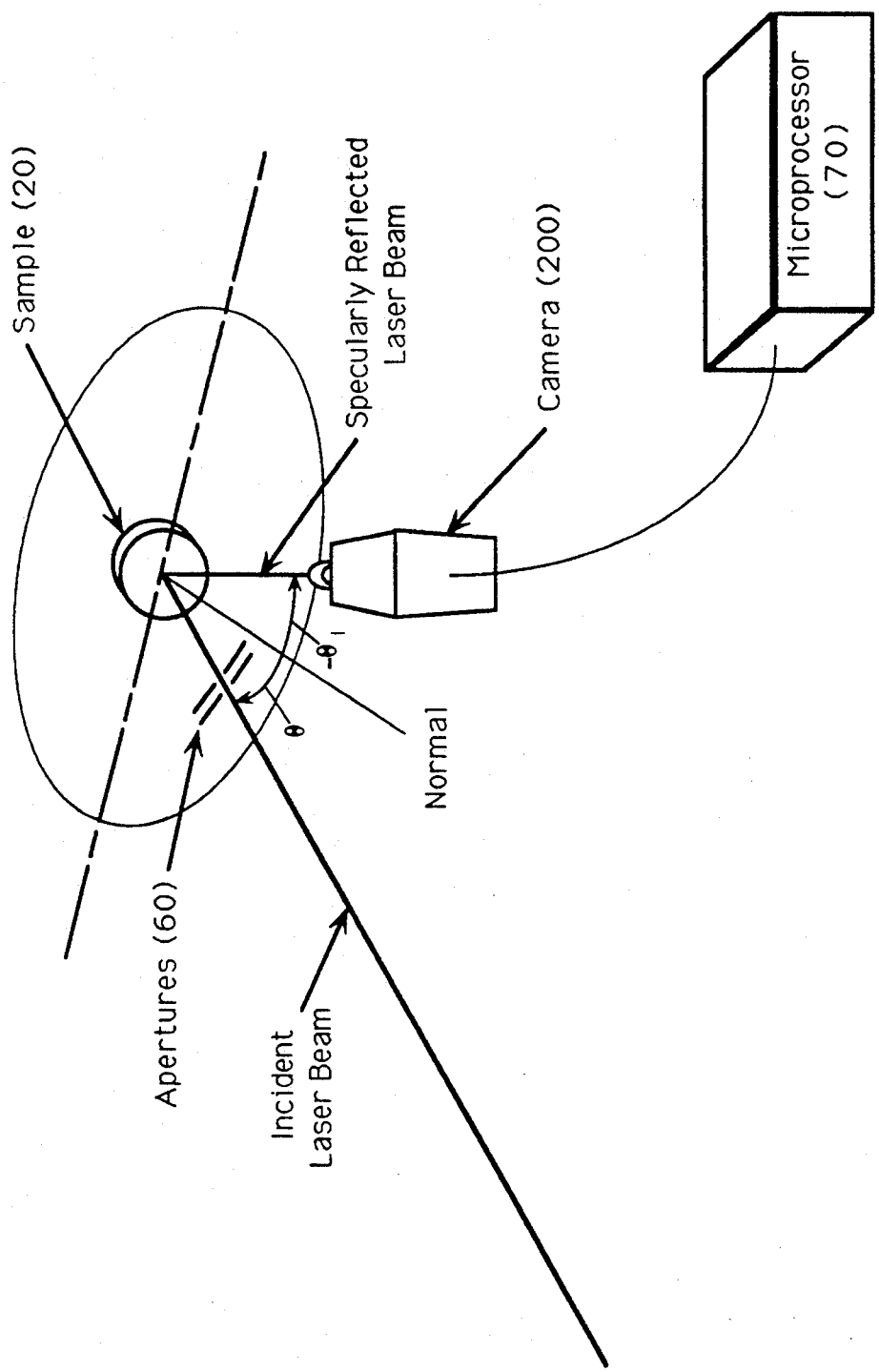
FIG. 3 is a pictorial diagram illustrating a prior art scatterometer system employing a camera as a detector for the characterization of near-angle scattered light.
Figure 4:
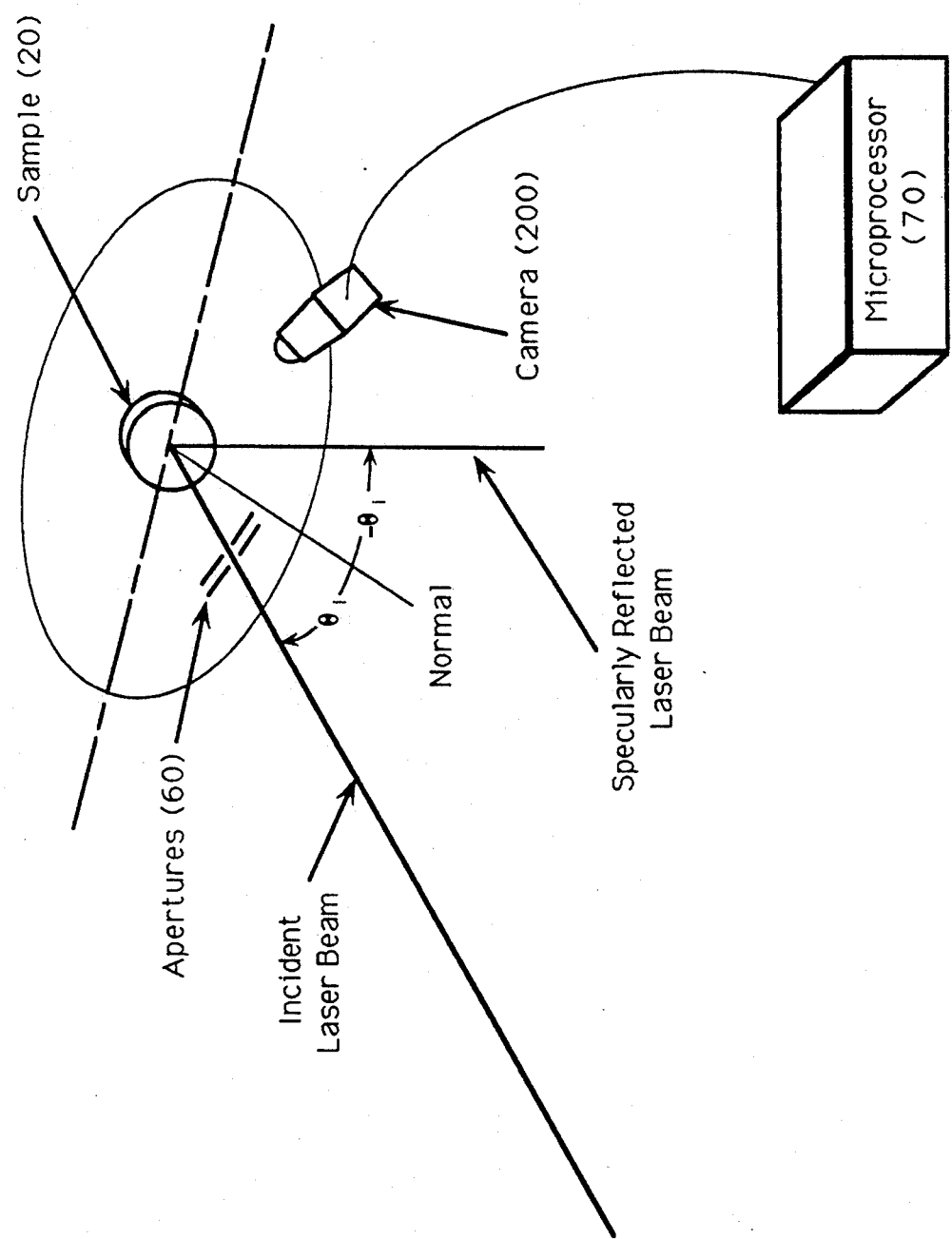
FIG. 4 is a pictorial diagram illustrating a prior art scatterometer system employing a camera as a detector for the characterization of large-angle scattered light.

Referring to FIGS. 1–4, there are shown several prior art scatterometer systems. FIG. 1 illustrates a scatterometer system employing a laser light beam incident on a point of a sample and a single light detector that is mechanically rotated or scanned in an arc contained in the plane of incidence. FIG. 2 illustrates a scatterometer system employing arrays of detectors located in an arc or line segment. FIGS. 3 and 4 illustrate scatterometer systems employing cameras arranged for the characterization of near-angle and large-angle scattered light, respectively. The systems shown in FIGS. 3 and 4 are significantly limited in the amount of scattered light that they are able to characterize compared to the total amount of light that is scattered from the sample due to their small angular fields of view. For example, if the cameras illustrated in those figures have a lens diameter of 50 mm, and the lens is located a distance of 30 cm from the sample, the solid angle over camera detects light scattered from the sample is approximately 0.022 steradians. This is less than 0.35% of the full region of space over which the sample scatters if the sample is not optically transmitting at the laser wavelength of interest, and less than 0.17% if the sample is transmitting and therefore scattering throughout all regions of space. This limitation, in turn, severely limits the capability of the scatterometer to fully characterize sample microstructure. Only a small range of spatial frequencies or spatial wavelengths of the sample microstructure are characterized. Scatterometers utilizing the prior art detection arrangements of FIGS. 3 and 4 have a small field of view and a small measurement bandwidth.

The present invention is directed to two-dimensional detectors or detector arrays for use in scatterometer systems. Any of a number of types of two-dimensional detector arrays may be employed, such as charge coupled detector (CCD) arrays, photomultiplier arrays, Si photodiode arrays, pyroelectric arrays, combinations of these arrays to form what is termed image enhanced detector arrays, vidicons, or other similar devices that may be used alone or in combination with other optical elements such as lenses, apertures, etc. to form what is commonly called a camera. The pixels of the detector arrays may have a rectangular symmetry, or they may have another convenient symmetry, such as circular or fan-shaped. In the description that follows, the chosen detector array, including any possible auxiliary optical elements, will be termed a camera. The camera measures light scattered from a sample which is illuminated with one or more beams of light. While these beams of light are described herein as originating from a laser, lamp sources may be suitable for providing a bright light. One example of a suitable lamp source is a Xenon short arc lamp. The incident and specularly reflected light beams from each light source define planes of incidence. The planes of incidence of the light beams are not required to be identical; the beams may be incident in different planes. The sample under investigation may comprise a solid, a liquid or gas fluid, or a fluid which contains particulates or specimens that are to be examined. If the sample is not a solid, it is necessary that it be contained within a vessel that substantially transmits the light beams used to illuminate the sample as well as the subsequently scattered light.

The camera may be interfaced to conventional processing circuitry. For example, the camera output may be connected to a frame grabber that permits further processing by a microprocessor. Simpler processing electronics may also be used to interface the camera to a microprocessor, or the camera output may be simply displayed on a video monitor without further processing. Of general interest is the two-dimensional map of the intensity of light scattered from the sample under investigation.

Figure 5A:
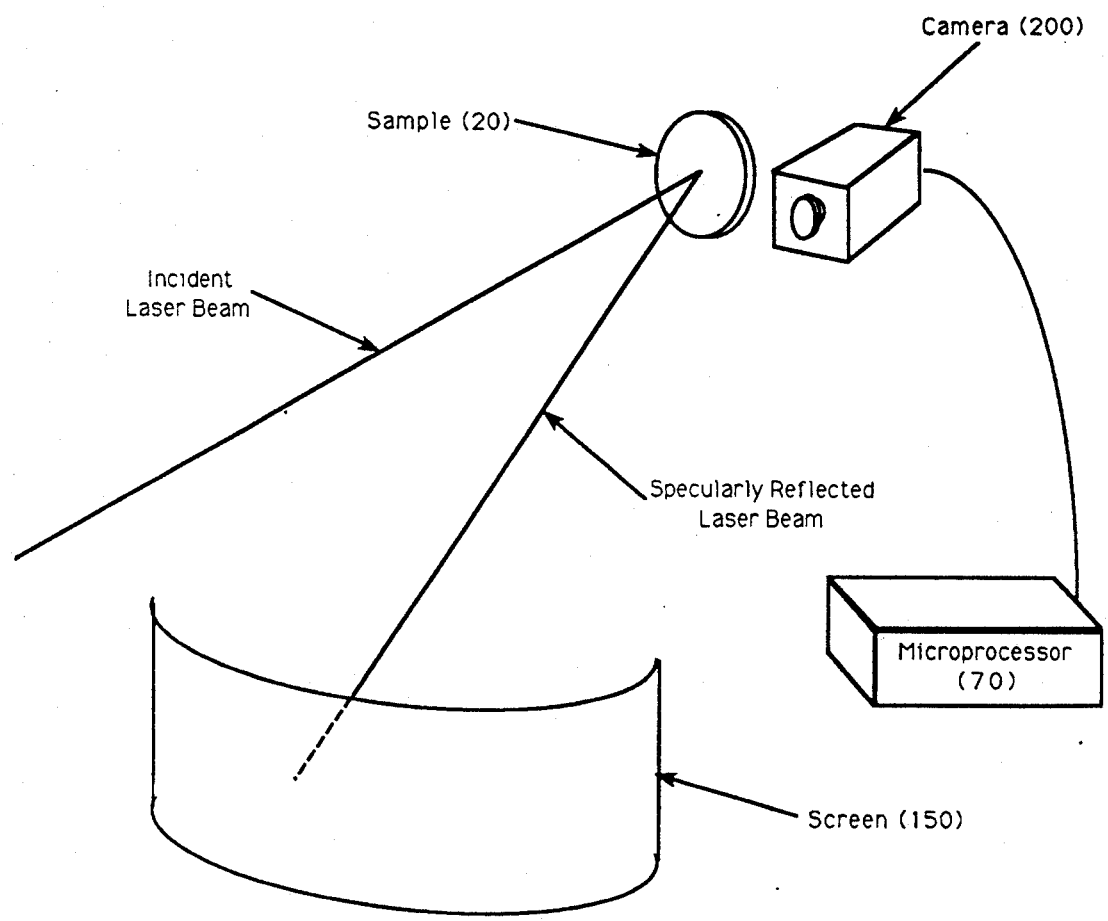
FIG. 5A is a pictorial diagram illustrating a two-dimensional scatterometer detector system constructed in accordance with the present invention in which a screen and a camera for imaging the screen are employed to characterize the scattered light in front of the sample.
Figure 5B:
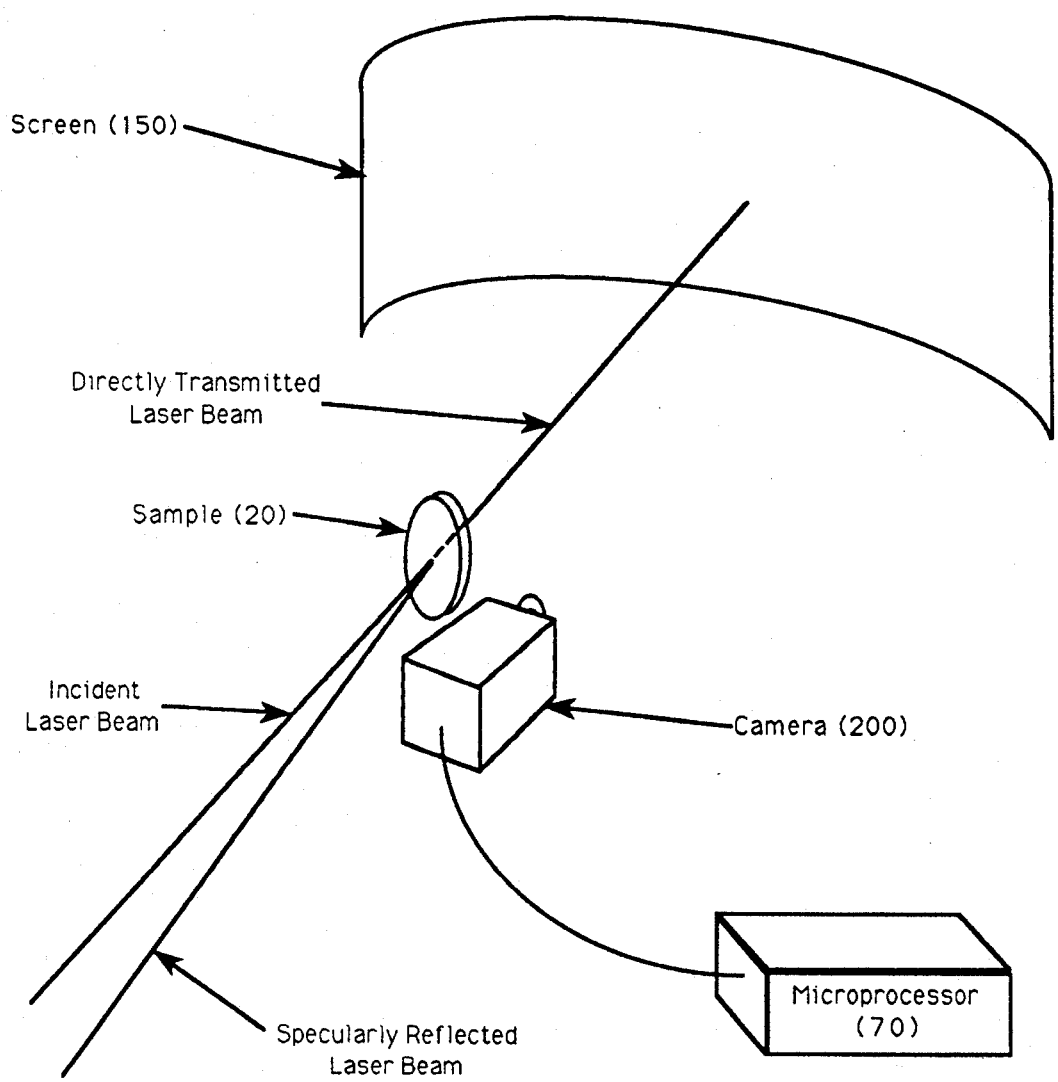
FIG. 5B is a pictorial diagram illustrating a two-dimensional scatterometer detector system constructed in accordance with the present invention in which a screen and a camera for imaging the screen are employed to characterize the scattered light behind the sample.
Figure 5C:
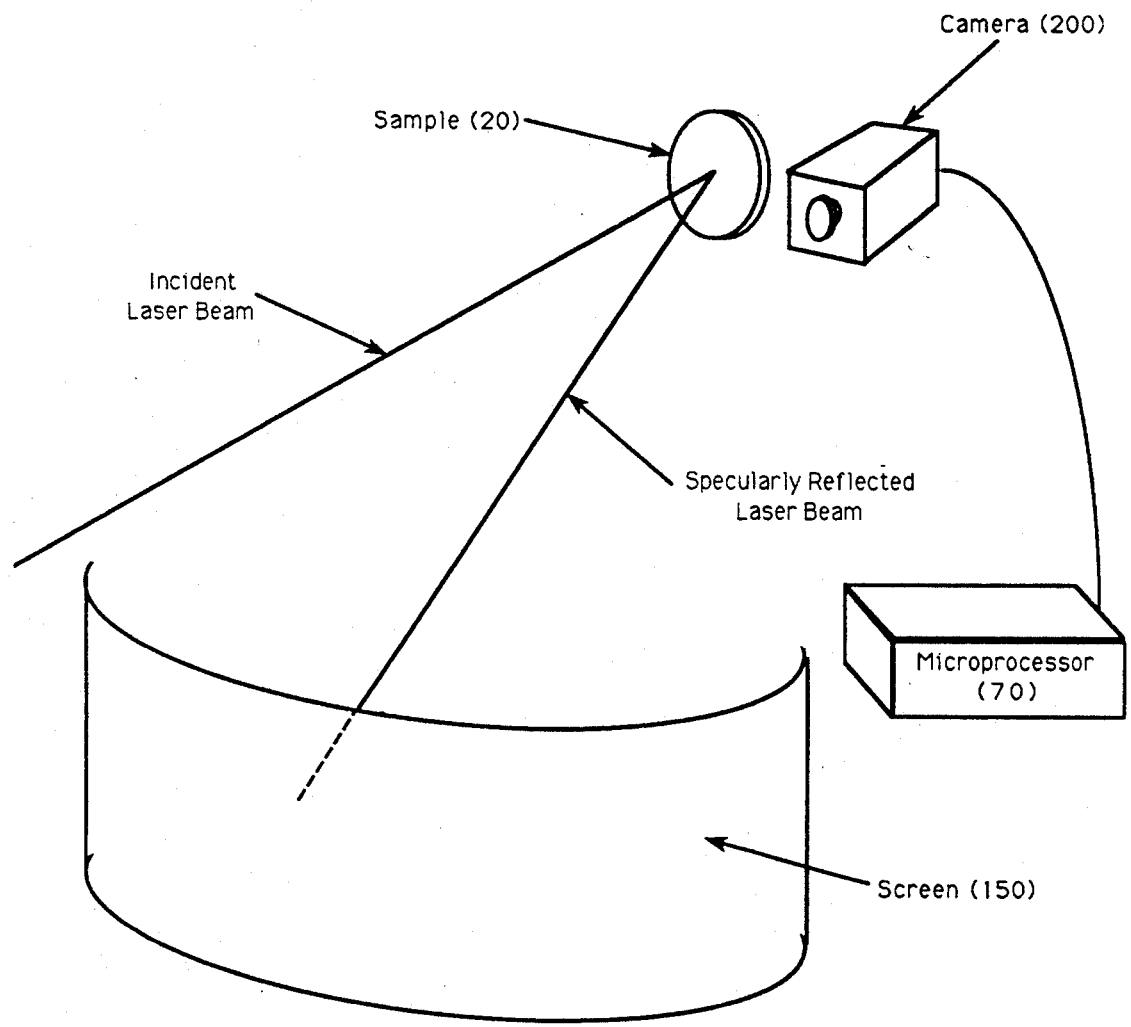
FIG. 5C is a pictorial diagram of the two-dimensional scatterometer detector system of FIG. 5A in which a larger screen is provided to improve the detection bandwidth.
Figure 5D:
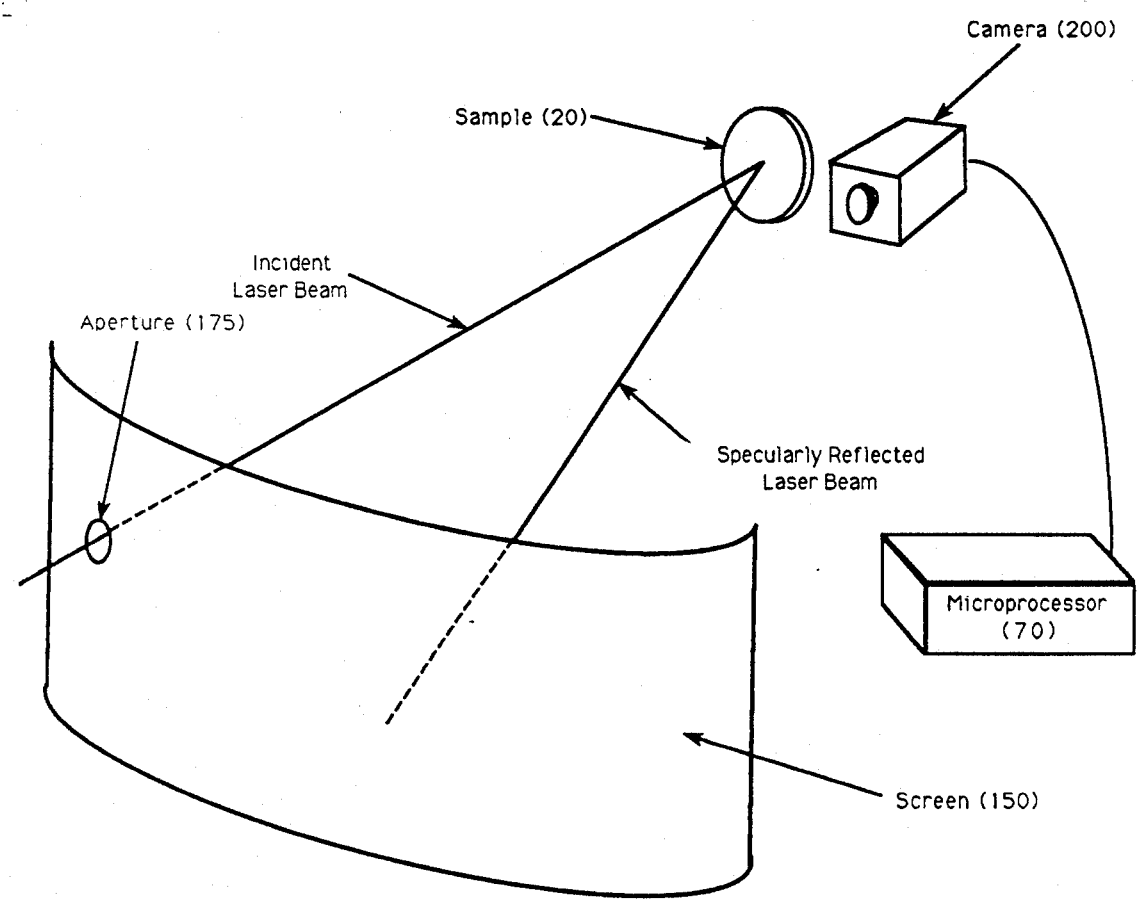
FIG. 5D is a pictorial diagram illustrating a two-dimensional scatterometer detector system constructed in accordance with the present invention in which an even larger screen is provided to permit passage of an incident laser beam through an aperture therein to thereby improve the bandwidth of the detector system.

Referring now to FIGS. 5A–D, there is illustrated a scatterometer detector system constructed in accordance with one embodiment of the present invention to provide an improved spatial frequency bandwidth measurement capability for characterizing optical scatter in two dimensions of space. A laser beam is arranged to be incident on a sample 20. A portion of the incident laser beam is reflected from the sample 20 as a specularly reflected laser beam. This specularly reflected light may strike a screen 150 that is placed in proximity to the sample 20, as illustrated in FIG. 5A, or the screen 150 may be oriented such that this specularly reflected beam does not strike the screen 150. A camera 200 is positioned to view the screen 150. The image from camera 200 yields a measurement of the light intensity pattern on the screen 150, resulting in a two-dimensional intensity map of the scattered light from the sample 20. The region of space in which the screen 150 is located, as illustrated in FIGS. 5A, 5C, and 5D, is considered to be in front of the sample 20.

If sample 20 is optically transmitting at the laser wavelength of interest, screen 150 may be positioned in the region of space behind sample 20, as illustrated in FIG. 5B. Both the scattered light in this region of space and the directly transmitted laser beam strike the screen 150. Camera 200 produces an image of the screen 150, thereby characterizing the light transmitted by the sample 20 in the same manner as previously described. Similarly, two or more screens and cameras may be arranged to monitor light in front of sample 20 and behind sample 20 by combining the detector arrangements illustrated in FIGS. 5A and 5B.

Screen 150 is preferably diffuse as opposed to specular in its optical scatter characteristics. Optimally, screen 150 has a Lambertian scatter characteristic such that it scatters light uniformly at all angles from its surface. This permits camera 200 to intercept and detect light from all points on screen 150 that are illuminated by light from sample 20. Screen 150 may also be constructed to have certain photochromic or pyrochromic properties, such as fluorescense at the laser wavelength of interest. The intensity of the emitted fluorescence at some point on screen 150 is dependent upon the intensity of the scattered light at that point. Camera 200 measures the intensity distribution of the fluorescence of screen 150, thereby yielding a two-dimensional map of the scattered light from sample 20. This arrangement may be particularly useful to detect ultraviolet light scattered from sample 20 at a wavelength at which camera 200 is not sensitive. Other photochromic or pyrochromic screen materials may find particular utility in characterizing infrared, near infrared, and ultraviolet wavelength light that is scattered by sample 20 but that cannot otherwise be detected by camera 200. The surface of screen 150 may be constructed of a material that changes optical properties, such as color or optical absorption, in a manner that is dependent upon the intensity of infrared light illuminating it. Exemplary of such materials are liquid crystals used in conjunction with mylar sheets available from Edmond Scientific, Barrington, N.J. Similarly, screen 150 may be constructed of electron trapping (ET) materials. These materials are used for observing infrared and near infrared laser emission, as they emit visible light when illuminated with the longer wavelength light. These materials are available from Quantex, Rockville, Md., for example. One form of ET material also emits visible light when illuminated with ultraviolet light and is therefore useful for detecting ultraviolet light scattered from sample 20. The chosen materials may, for example, be deposited on the surface of a glass or plastic surface to form screen 150.

The physical size of screen 150 determines the amount of light from sample 20 intercepted thereby. If camera 200 is capable of imaging the entire area of screen 150, increasing the size of screen 150, while maintaining the same separation from the sample 20, such that more of the light scattered from sample 20 is intercepted, thereby increases the measurement bandwidth of the overall scatterometer system. This is illustrated by comparing FIGS. 5A, 5C, and 5D. Screen 150 illustrated in FIG. 5C intercepts more light from sample 20 that that of FIG. 5A. Similarly, screen 150 of FIG. 5D intercepts more light than that illustrated in FIG. 5C. The configuration illustrated in FIG. 5C therefore exhibits a larger measurement bandwidth than that of FIG. 5A, and the configuration illustrated in FIG. 5D exhibits a larger measurement bandwidth than that of FIG. 5C. The large size of screen 150 in FIG. 5D requires that an aperture 175 be provided therein to permit passage of the incident laser beam.

An optimal geometric configuration for screens 150 illustrated in FIGS. 5A–D is one comprising a portion of a sphere having its center of curvature coincident with the point on sample 20 illuminated by the incident laser beam. In addition, the radius of curvature of screen 150 is optimally such that the specularly reflected beam from sample 20 is focused on screen 150. In this manner, the surface of screen 150 is located such that the scattered light from sample 20 represents the Fourier transform properties of the microstructure of sample 20 if sample 20 is optically smooth and reflecting. If sample 20 is not optically smooth and reflecting, it is nevertheless desirable to maintain the arrangement as described above. The surface of screen 150 is thus said to be in the Fourier transform space of the imaging system. The details of such properties of imaging systems are well known. The two-dimensional measurement of the scattered light intensity on the surface of screen 150 characterizes the sample microstructure in two dimensions of spatial frequency of the sample microstructure. This is analogous to the one-dimensional characterization of scattered light resulting from use of the prior art scatterometer illustrated in FIG. 1 in which the detector path defines a circular arc in which the specularly reflected beam from the sample is brought to a focus by the optical system of the scatterometer. This circular arc is known as the Fourier transform arc.

While it is desirable that screens 150 of FIGS. 5A-D be shaped to be a portion of a sphere, it is not essential that they be so shaped. For example, the screen 150 may be flat or have some other curved shape. Variations in the shape of screen 150 may be convenient for fabrication purposes. Similarly, it is not essential that the specularly reflected and directly transmitted light from the sample 20 come to a focus on the screen.

Figure 6A:
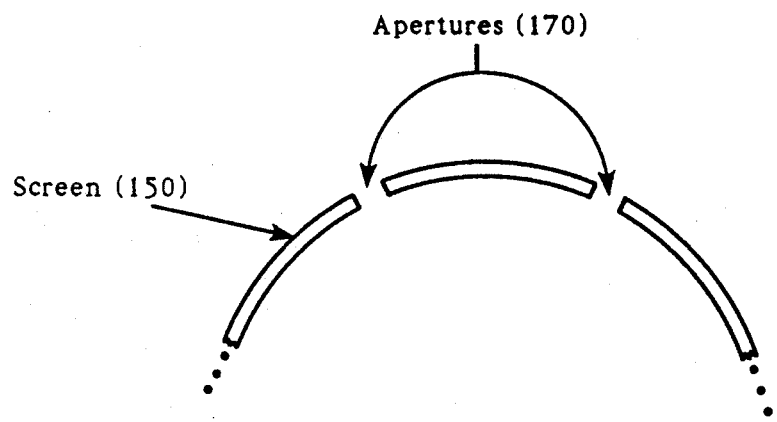
FIG. 6A is a sectional diagram of a portion of a screen that may be employed in the two-dimensional scatterometer detector system of the present invention in which several apertures are provided to permit high intensity light to exit the screen.
Figure 6B:
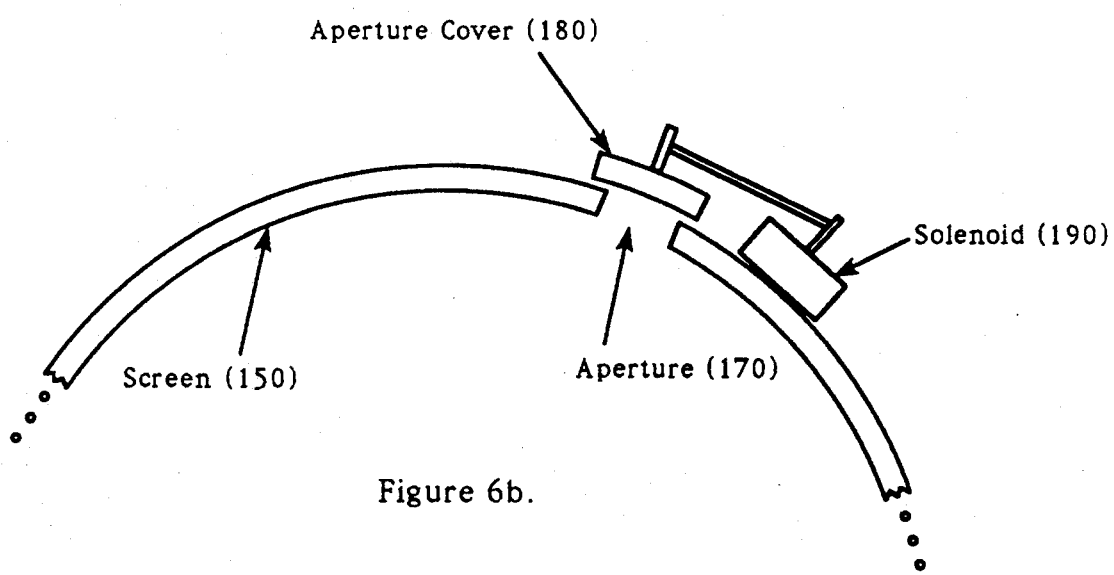
FIG. 6B is a sectional diagram of a portion of the screen employed in the two-dimensional scatterometer detector system of FIG. 5D in which a movable aperture cover is provided to selectively cover the aperture in the screen.

Referring now to FIGS. 6A-B, there is shown a sectional diagram of a portion of screen 150 of FIGS. 5A-D in which several apertures 170 have been provided. Apertures 170 are located in regions of screen 150 that are illuminated with light which is significantly more intense than at other regions. These regions of screen 150 include, for example, those illuminated by the specularly reflected or directly transmitted laser beams and those illuminated by light which is diffracted from one or more periodic structures on sample 20 that act to strongly diffract the incident light. Examples of samples 20 that possess periodic structure include diffraction gratings, crystalline material which has repetitive defects such as slip planes in one or two dimensions, finely machined surfaces such as diamond turned optics, surfaces which are generated by passing material through rollers, computer hard disks and other magnetic storage media having a grooved structure, and complex microelectronic circuits such as memories, gate arrays, microprocessors, and similar circuitry. The apertures 170 permit the intense light to pass through screen 150 and therefore not be detected by camera 200. In this manner, the operating conditions for camera 200, such as f-stop, can be adjusted for optimal characterization of the light at regions of the screen 150 that are less intensely illuminated.

Referring now to FIG. 6B, it is shown that one or more of the apertures 170 in screen 150 may be covered with a material having optical properties similar to those of the remainder of screen 150, thereby making screen 150 appear as though aperture 170 is not present. A movable cover 180 is provided for covering and uncovering aperture 170. Cover 180 may be moved by any of a number of conventional mechanisms including, for example, a solenoid 190 that is adapted to move cover 180 either linearly or rotationally into position over an associated one of the apertures 170. The more intensely illuminated regions of screen 150 may then be characterized using camera 200 with operating conditions appropriate for the greater intensity of the light with one or more of the covers 180 positioned over their associated apertures 170. The f-stop of camera 200 is easily changed manually or by using a small motor mounted within a camera lens assembly. Electronic shutter control may also be employed for controlling camera conditions. One or more covers 180 may then be moved to uncover the respective apertures 170, and the camera operating conditions may then be adjusted as appropriate for characterizing regions of screen 150 that are less intensely illuminated. Similarly, the multiple-step characterization described above, with and without aperture covers 180 in place over their associated apertures 170, may be accomplished in conjunction with the filter wheel assembly described in pending application Ser. No. 474,356 to adjust the intensity of the illuminating laser beam and to, in turn, adjust the intensity of the illuminated regions of the screen 150. The motors, shutters, solenoids, and filter wheel are in turn controlled by the scatterometer system microprocessor 70.

Aperture cover 180 may comprise two or more sections, each having the same optical scatter properties as screen 150. For example, one section of aperture cover 180 may be circular, while the remaining section or sections may be annular. Each of the sections may be controlled separately by solenoid 190 to provide, in effect, an aperture 170 of variable diameter.

The samples under investigation having periodic structure, as discussed above, may be examined using screen 150 in a simper configuration without the presence of aperture 170. The filter wheel described in application Ser. No. 474,356 may be employed to provide characterization of regions of screen 150 that are strongly illuminated by scattered light as well as regions weakly illuminated. When characterizing the weakly illuminated regions of screen 150 with the filter wheel providing a correspondingly low attenuation of the incident laser beam, the more strongly illuminated regions of screen 150 may be saturating portions of the camera detector array. These saturated portions of the array can be neglected when analyzing the image received from camera 200.

Figure 7A:
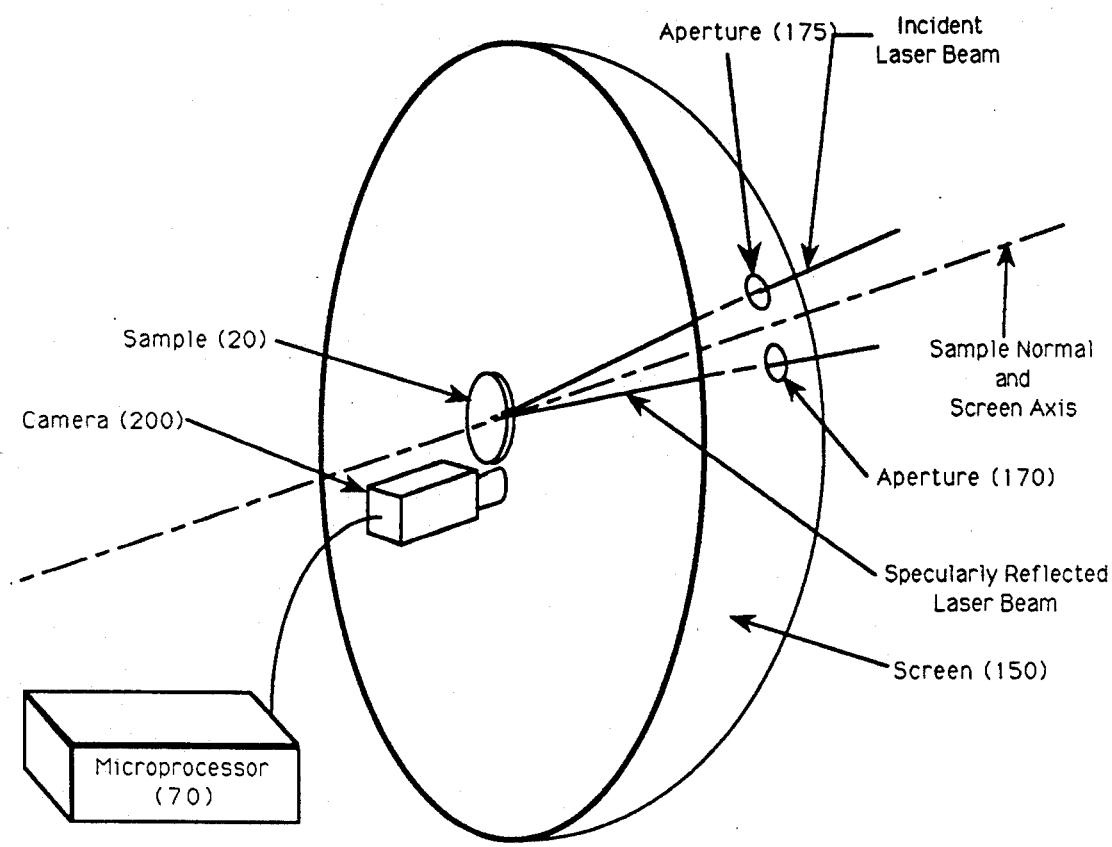
FIG. 7A is a pictorial diagram illustrating a two-dimensional scatterometer detector system constructed in accordance with the present invention in which a hemispherically-shaped screen is provided with an aperture at or near the axis of the screen to permit passage of the incident laser beam through the screen.
Figure 7B:
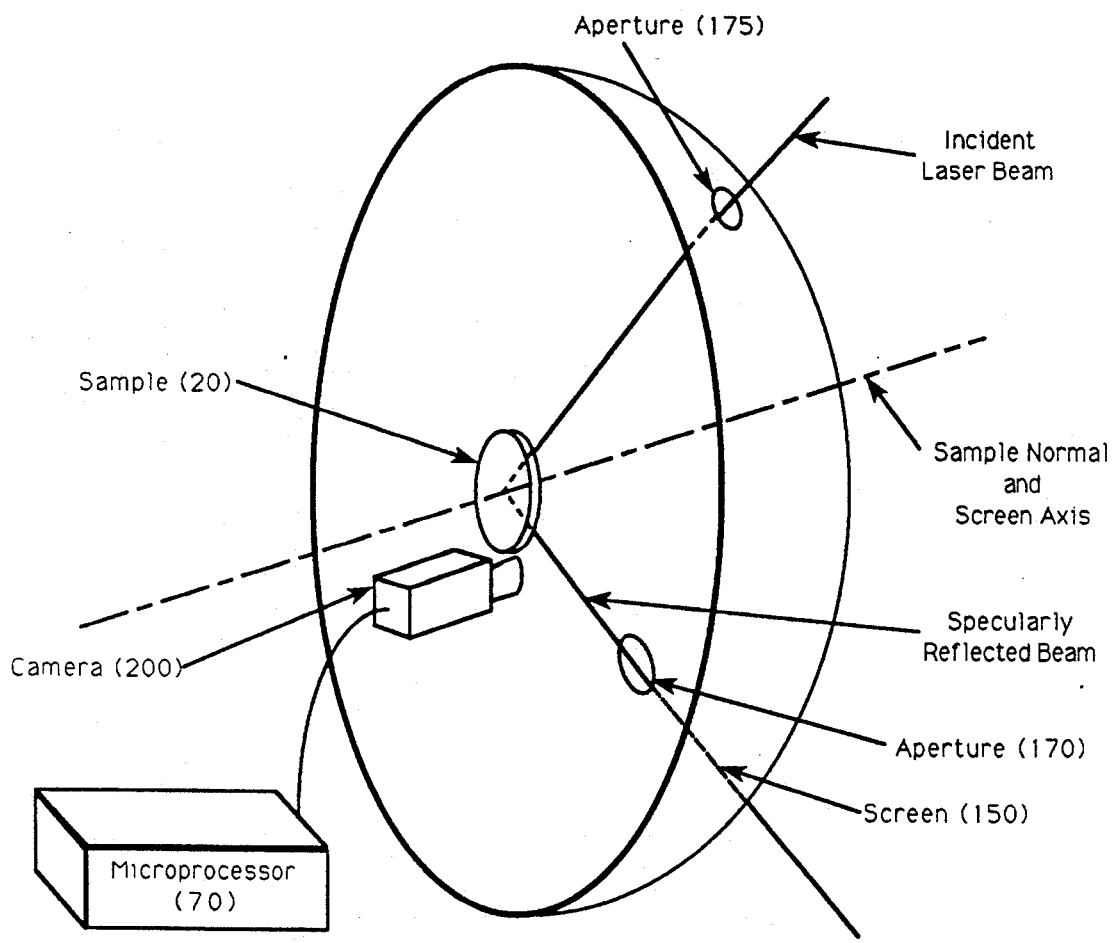
FIG. 7B is a pictorial diagram illustrating a two-dimensional scatterometer detector system constructed in accordance with the present invention in which a hemispherically-shaped screen is provided with apertures significantly removed from the axis of the screen to permit passage of the incident and specularly reflected laser beams through the screen.

Referring now to FIGS. 7A-B, there is illustrated an embodiment of the present scatterometer detector system in which screen 150 is practically hemispherical in shape, thereby collecting virtually all of the light scattered in front of sample 20. The imaging systems illustrated in FIGS. 7A-B then enable camera 200 to characterize the intensity distribution of the scattered light at all points of the hemispherical screen 150, throughout 2 pi (6.28) steradians of space. This provides a measurement system having a maximum spatial frequency and spatial wavelength bandwidth. Arrangements similar to those illustrated in FIGS. 7A-B, in which camera 200 is positioned behind sample 20, may be used to characterize scattered light in this region of space if sample 20 is optically transmitting at the wavelength of interest.

In the embodiment of FIG. 7A, camera 200 is equipped with a lens system having a large field of view of 150 degrees or more, for example. Such a lens is sometimes referred to as a fisheye lens or wide angle lens and is a commonly available element for use with camera systems. Implementation of the embodiment of FIG. 7A typically involves positioning the lens of camera 200 and sample 20 near the center of curvature of screen 150. Sample 20 and the top of the lens of camera 200 may be positioned in a plane that also contains the center of curvature of screen 150, as shown in FIG. 7A. The plane would also contain the periphery of the hemispherical screen 150, or it would be parallel to the periphery if screen 150 is not exactly hemispherical in shape. Sample 20 and the lens of camera 200 would be separated laterally approximately the same distance from the center of curvature of screen 150. In this manner, the scattered light from sample 20 is in Fourier space on the surface of screen 150, as described above. This arrangement also facilitates proper imaging of the entire screen area. Additional configurations are possible in which the lens of camera 200 and sample 20 are not in the same plane as that containing the center of curvature of screen 150. Sample 20 and the lens of camera 200 may both be slightly displaced vertically a small amount such that they are both closer to screen 150. Alternatively, they may both be displaced vertically such that they are both further removed from screen 150. Additional configurations include one in which sample 20 is positioned closer vertically to screen 150 and the top of the lens of camera 200 is positioned further vertically from screen 150, and vice versa. These additional configurations may be employed, for example, to optimize light collection or imaging, or to accommodate positioning of large samples, such as semiconductor wafers.

The embodiments of the invention illustrated in FIG. 7A illustrates the incident laser beam entering screen 150 through an aperture 175 near the axis of screen 150, in which the angle of incidence $\theta_i$ of the incident laser beam is approximately zero. More than one incident wavelength of light may be used to illuminate the sample for the reasons discussed in U.S. Pat. No. 4,710,642 and application Ser. No. 474,356. The multiple wavelengths may originate from more than one laser, or they may originate from a single laser having a multiple wavelength output.

In the embodiment of the present invention illustrated in FIG. 7B, the incident laser beam enters screen 150 through an aperture 175 that is significantly removed from the axis of screen 150, such that $\theta_i$ is significantly larger than zero. This change in $\theta_i$ will influence the bandwidth of the measurement system, as defined by the grating equation described in U.S. Pat. No. 4,710,642.

FIG. 7B also illustrates a corresponding aperture 170 in screen 150 through which the specularly reflected beam is permitted to exit. Aperture 170 may also be equipped with an aperture cover 180 as described above in connection with FIG. 6B. Screen 150 may include more than one aperture 170 through which several incident laser beams pass. One of the apertures 175 may be on or near the axis of screen 150, and the other apertures 175 may be significantly removed from that axis. Laser output of a single wavelength is permitted to enter one or more of the apertures 175 to illuminate sample 20 at one or more angles of incidence $\theta_i$. Alternatively, the incident laser beams passing through apertures 170 may be at different wavelengths originating from one or more lasers.

Illumination of sample 20 at different laser wavelengths causes different scatter patterns to occur on screen 150. Similarly, illumination of sample 20 at different angles $\theta_i$, either with laser output of one wavelength or multiple wavelengths causes different scatter patterns on screen 150. The illumination of sample 20 at different angles $\theta_i$ or different wavelengths of light may be achieved simultaneously or sequentially. Camera 200 may thereby characterize the intensity patterns of the scattered light produced on screen 150 by illumination of sample 20 at multiple angles $\theta_i$ and multiple wavelengths of light.

Each of apertures 175 in screen 150, illustrated in FIGS. 7A-B, may have an associated aperture 170 appropriately located in screen 150 to pass the specularly reflected beam. The apertures 170 may also be equipped with aperture covers 180, as illustrated in FIG. 6B.

Figure 8A:
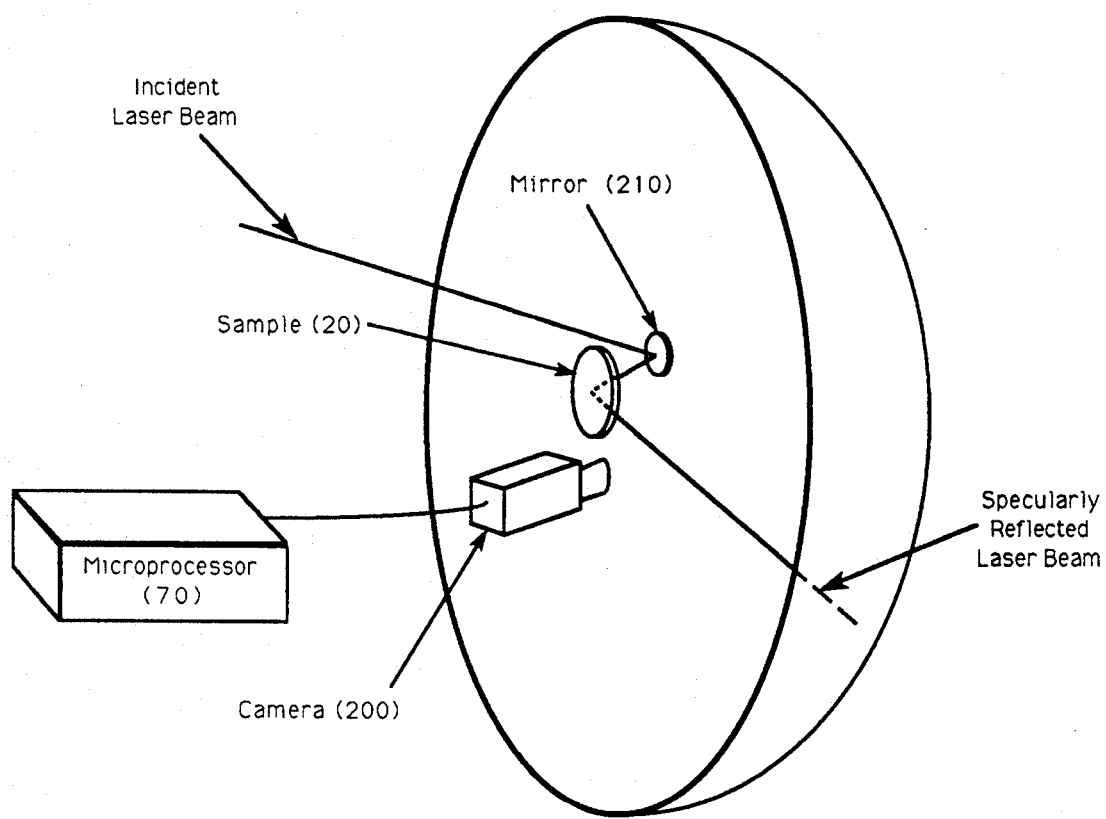
FIG. 8A is a pictorial diagram illustrating a two-dimensional scatterometer detector system constructed in accordance with the present invention in which a mirror is provided to direct the incident laser beam onto the sample.
Figure 8B:
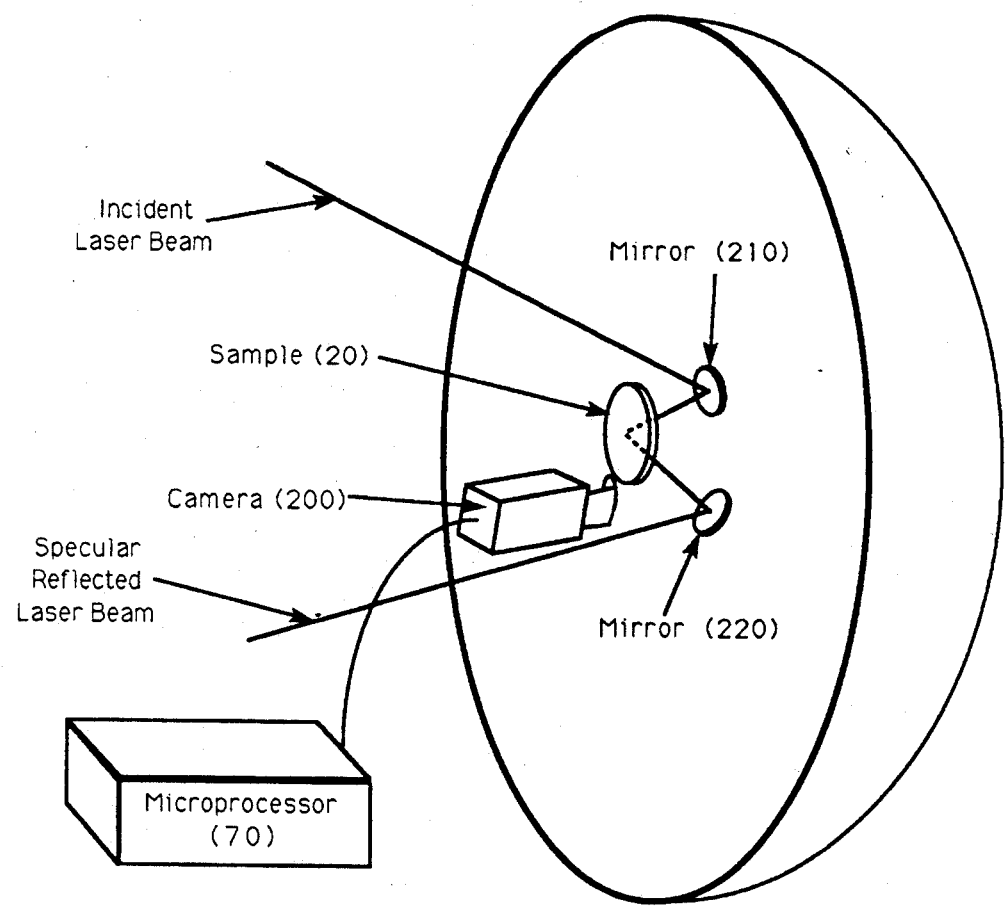
FIG. 8B is a pictorial diagram illustrating a two-dimensional scatterometer detector system constructed in accordance with the present invention in which two mirrors are provided to direct the incident and specularly reflected laser beams onto and away from the sample.

Referring now to FIG. 8A, there is illustrated a further embodiment of the present invention for directing the incident laser beam onto sample 20. The incident laser beam is incident from below sample 20 to a mirror 210 that is arranged at such an angle as to direct the incident laser beam onto sample 20. Similarly, an optical fiber or light guide may be employed to serve the function of mirror 210. The specularly reflected beam can strike screen 150 and be analyzed as described above. This embodiment may also include an aperture 170 in screen 150, as well as an aperture cover 180, as previously described. Optionally, the specularly reflected beam may be deflected by another mirror 220 and directed out of the optical system, as illustrated in FIG. 8B. Mirrors 210, 220 and fiber optic elements may be constructed in such a manner that they obscure only an insignificant portion of screen 150 to block light scattered from sample 20. Optionally, mirror 220 may be replaced with a suitable beam dump to eliminate the specularly reflected beam.

Figure 9:
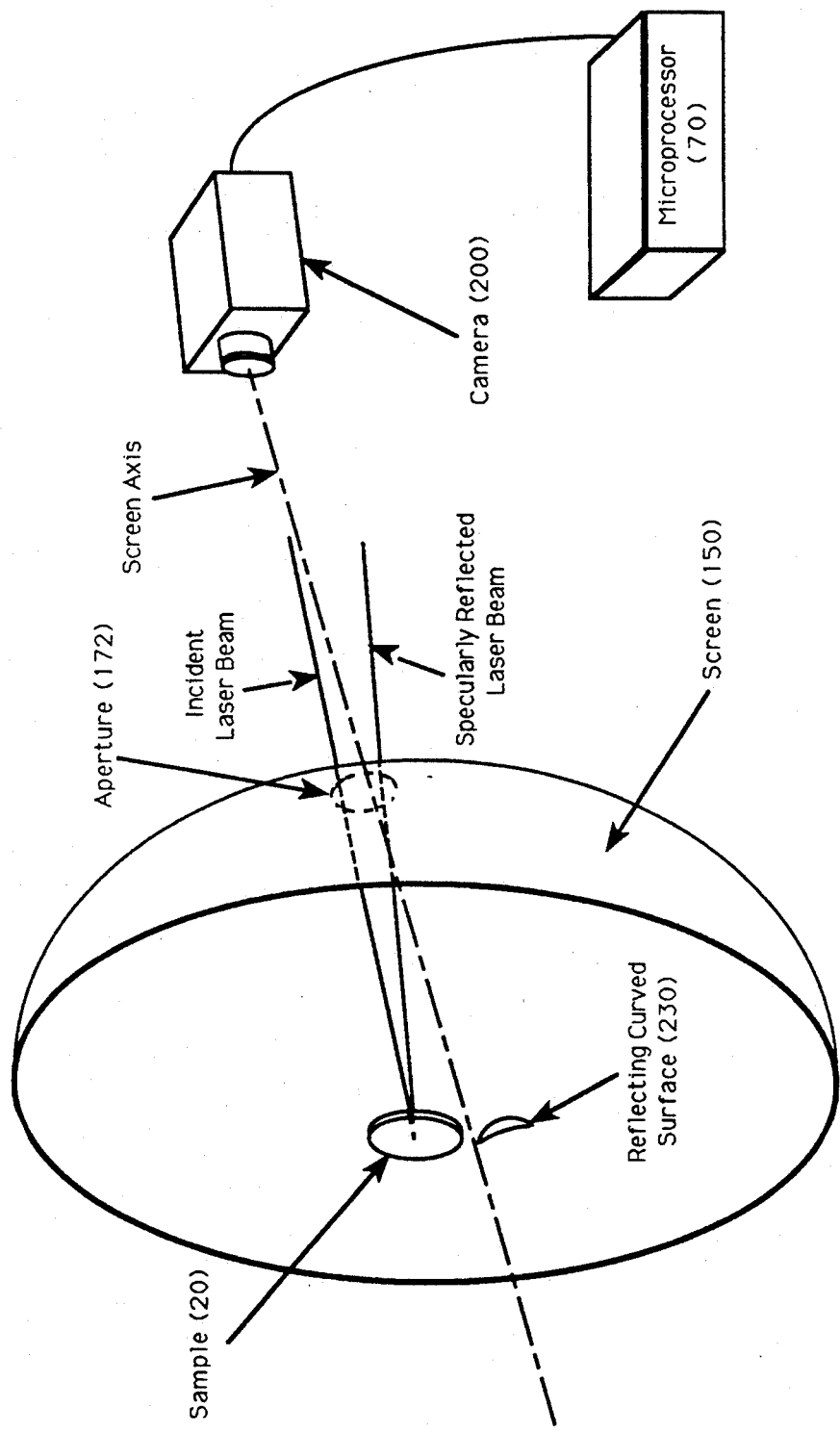
FIG. 9 is a pictorial diagram illustrating a two-dimensional scatterometer detector system constructed in accordance with the present invention in which a convex specular reflecting element is provided to direct light from the screen to the camera.

Referring now to FIG. 9, there is shown an embodiment of the present invention in which a specularly reflecting, generally convex curved surface 230 is placed near the center of curvature of screen 150 and the sample 20. Element 230 serves to direct light from all regions of screen 150 through an aperture 172 in screen 150 to camera 200. The lens of camera 200 images the screen 150 on the detector of camera 200. The choices for locating reflecting curved surface 230 are similar to those discussed for placement of the camera lens discussed previously in connection with FIG. 7A. That is, the reflecting curved surface 230 may be placed with its center of curvature located a small distance laterally or vertically removed from the center of curvature of screen 150 to accommodate positioning of sample 20. Only a fraction of the reflecting curved surface 230 is required for imaging screen 150 such that the light rays from the bottom extremity of screen 150 are deflected to the lens of camera 200 to be imaged. For example, if the reflecting curved surface 230 is spherical in shape, it is not necessary for the entire sphere to be present. The size of the reflecting curved surface 230 is typically between 1 and 10 cm in lateral extent, with a surface that can be spherical or some other convex shape that produces optimal imaging of screen 150 by camera 200. A spherical surface is most economically available, however. In the embodiment of FIG. 9, the laser beam enters and exits the same aperture 172 that is located on the axis of screen 150. Aperture 172 also allows light to pass through screen 150 to camera 200. Positioning of the various structural elements as illustrated in FIGS. 7A-B and 8A-B may also be accomplished in connection with the embodiment illustrated in FIG. 9. Thus, the entrance apertures 175 and exit apertures 170 through which the incident laser beam passes and the aperture 172 through which the specularly reflected beam passes may be separately located at different angles with respect to the axis of screen 150. Similarly, these various apertures may be utilized in a combination in which one aperture is employed to pass the specularly reflected beam and also to act as either or both the entrance and exit aperture for the incident laser beam.

Figure 10:
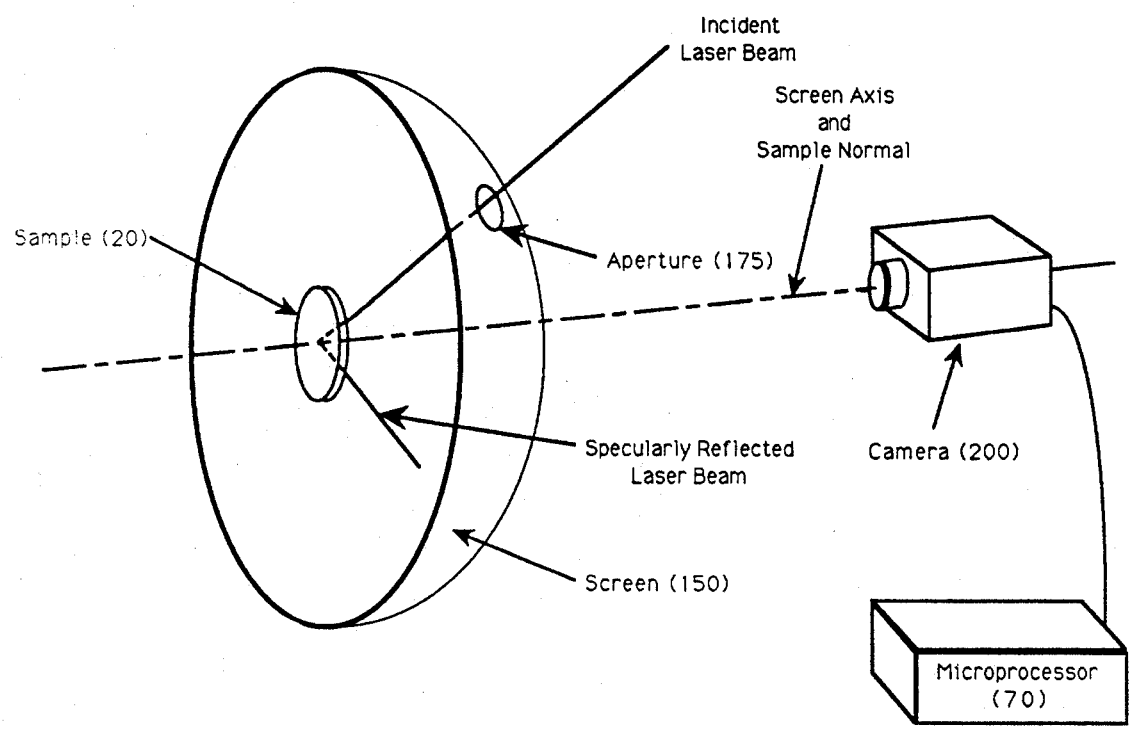
FIG. 10 is a pictorial diagram illustrating a two-dimensional scatterometer detector system constructed in accordance with the present invention in which the sample is located on one side of the screen and the camera used to view the scattered light appearing on the screen is located on the oppposite side of the screen.

Referring now to FIG. 10, there is shown an embodiment of the present invention in which camera 200 is significantly removed from sample 20. Camera 200 is located proximate the side of screen 150 opposite to that of sample 20. Thus, the pattern on screen 150 is viewed by camera 200 in transmission through the translucent material comprising screen 150. This arrangement reduces the constraints of sample size and location by locating camera 200 removed from sample 20, thereby facilitating automated handling of sample 20. The details of laser illumination discussed above are applicable to the embodiment of FIG. 10. In particular, the incident laser beam may be directed onto sample 20 by passing it through aperture 175 in screen 150. Aperture 175 may be located on or close to the axis of screen 150, or it may significantly removed from the axis of screen 150 such that the angle of incidence $\theta_i$ is large. Alternatively, the incident laser beam may be directed onto sample 20 by utilizing mirrors 210, fiber optics or waveguides. The same wavelength of light may be used to illuminate sample 20 at one or more angles of incidence $\theta_i$, or one or more incident laser beams of different wavelengths may be used to illuminate sample 20 at one or more angles of incidence $\theta_i$. Apertures 170 and aperture covers 180 may also be utilized in screen 150 as discussed above to accommodate the specularly reflected laser beam or scattered light which is intense.

We claim:

1. An optical scatterometer system comprising:
   a sample material having periodic and diffractive microstructure characteristics to be analyzed;
   light source means for transmitting an incident light beam to illuminate a point on the sample material;
   screen means positioned to receive and display a pattern representative of light specularly reflected from said sample material and light scattered from said sample material, said screen means including one or more apertures for passing said incident light beam and a selected one or both of said light specularly reflected from said sample material and a portion of said light scattered from said sample material, to thereby prevent the selected one or both of said light specularly reflected from said sample material and said portion of said light scattered from said sample material from being received and displayed on said screen means;
   camera means positioned to record the pattern displayed on said screen means; and
   microprocessor means coupled to said camera means for processing electrical signals received therefrom to provide a two-dimensional intensity distribution of the pattern recorded by said camera means, said two-dimensional intensity distribution being indicative of the periodic and diffractive microstructure characteristics of said sample material.

2. An optical scatterometer system is in claim 1 wherein said screen means is shaped to form a curved surface to increase its light gathering capabilities and to thereby increase a bandwidth characteristic of the optical scatterometer system.

3. An optical scatterometer system as in claim 1 wherein said screen means is shaped to form a portion of a sphere.

4. An optical scatterometer system as in claim 1 wherein said screen means is positioned between said sample material and said light source means.

5. An optical scatterometer system as in claim 1 wherein said sample material is positioned between said screen means and said light source means.

6. An optical scatterometer system as in claim 1 wherein said screen means comprises a material having approximately Lambertian optical scattering properties.

7. An optical scatterometer system as in claim 1 wherein said screen means comprises a material that fluoresces at a wavelength of said incident light beam.

8. An optical scatterometer system as in claim 1 wherein said screen means comprises an electron trapping material.

9. An optical scatterometer system as in claim 1 wherein said screen means comprises a photochromic material.

10. An optical scatterometer system as in claim 1 wherein said screen means comprises a pyrochromic material.

11. An optical scatterometer system as in claim 1 further comprising removable aperture cover means for covering a selected portion of each of said one or more apertures.

12. An optical scatterometer system as in claim 1 wherein said one or more apertures are positioned at one or more selected corresponding angles of incidence with respect to an axis of said screen means.

13. An optical scatterometer system as in claim 1 wherein said incident light beam is transmitted at one or more selected angles of incidence with respect to an axis of said screen means.

14. An optical scatterometer system as in claim 1 wherein:
   said incident light beam is transmitted at one or more selected angles of incidence with respect to an axis of said screen means; and
   said incident light beam is transmitted at one or more selected wavelengths.

15. An optical scatterometer system as in claim 1 wherein:
   said incident light beam is transmitted simultaneously at a plurality of selected angles of incidence with respect to an axis of said screen means; and
   said incident light beam is transmitted simultaneously at a plurality of selected wavelengths.

16. An optical scatterometer system as in claim 1 wherein:
   said incident light beam is transmitted sequentially at a plurality of selected angles of incidence with respect to an axis of said screen means; and
   said incident light beam is transmitted sequentially at a plurality of selected wavelengths.

17. An optical scatterometer system as in claim 1 wherein said light source means comprises a laser.

18. An optical scatterometer system as in claim 1 wherein:
   said screen means is positioned between said sample material and said light source means;
   said screen means is constructed of a material that permits the pattern displayed thereon to be viewed from a side of the screen opposite said sample material; and
   said camera means is positioned on a side of said screen means opposite said sample material.

19. An optical scatterometer system as in claim 1 wherein said camera means and said sample material are both positioned on one side of said screen means.

20. An optical scatterometer system comprising:
   a sample material having periodic and diffractive microstructure characteristics to be analyzed;
   light source means for transmitting an incident light beam to illuminate a point on the sample material;
   screen means positioned between said sample material and said light source means to receive and scatter a pattern representative of light specularly reflected from said sample material and light scattered from said sample material, said screen means including an aperture therein through which said incident light beam is directed to illuminate said point on said sample material;

camera means positioned on the same side of said screen means as said light source means;

specularly reflecting curved element positioned on the same side of said screen means as said sample material for directing light scattered from said screen means through said aperture to said camera means for recording thereby; and microprocessor means coupled to said camera means for processing electrical signals received therefrom to provide a two-dimensional intensity distribution of the light scattered from said screen means and directed through said aperture by said specularly reflecting curved element that is recorded by said camera means, said two-dimensional intensity distribution being indicative of the periodic and diffractive microstructure characteristics of said sample material.

21. An optical scatterometer system comprising:

a sample material having periodic and diffractive microstructure characteristics to be analyzed;

light source means for transmitting an incident light beam to illuminate a point on the sample material;

reflector means positioned for receiving said incident light beam and for directing it onto said sample material to illuminate said point on said sample material and for receiving light specularly reflected from said sample material and for directing said light specularly reflected from said sample material away from said optical scatterometer system;

screen means positioned to receive and display a pattern representative of light scattered from said sample material;

camera means positioned to record the pattern displayed on said screen means; and microprocessor means coupled to said camera means for processing electrical signals received therefrom to provide a two-dimensional intensity distribution of the pattern recorded by said camera means, said two-dimensional intensity distribution being indicative of the periodic and diffractive microstructure characteristics of said sample material.

22. An optical scatterometer system as in claim 21 wherein said reflector means comprises a mirror.

23. An optical scatterometer system as in claim 21 wherein said reflector means comprises an optical fiber.

24. An optical scatterometer system comprising:

a sample material having periodic and diffractive microstructure characteristics to be analyzed;

light source means for transmitting an incident light beam to illuminate a point on the sample material;

reflector means positioned for receiving said incident light beam and for directing it onto said sample material to illuminate said point on said sample material;

additional reflector means for receiving light specularly reflected from said sample material and for directing said light specularly reflected from said sample material away from said optical scatterometer system;

screen means positioned to receive and display a pattern representative of light scattered from said sample material;

camera means positioned to record the pattern displayed on said screen means; and microprocessor means coupled to said camera means for processing electrical signals received therefrom to provide a two-dimensional intensity distribution of the pattern recorded by said camera means, said two-dimensional intensity distribution being indicative of the periodic and diffractive microstructure characteristics of said sample material.

25. An optical scatterometer system as in claim 24 wherein said additional reflector means comprises a beam dump.

26. An optical scatterometry process for analyzing periodic and diffractive microstructure characteristics of a sample material, the process comprising the steps of:

transmitting an incident light beam to illuminate a point on the sample material;

positioning a screen to receive and display a pattern representative of light specularly reflected from the sample material and light scattered from the sample material, the screen including one or more apertures therein for passing the incident light beam and a selected one or both of the light specularly reflected from the sample material and a portion of the light scattered from the sample material, to thereby prevent the selected one or both of the light specularly reflected from the sample material and said portion of the light scattered from the sample material from being received and displayed on the screen;

recording the pattern displayed on the screen; and processing information representative of the pattern recorded to provide a two-dimensional intensity distribution of the pattern recorded, the two-dimensional intensity distribution being indicative of the periodic and diffractive microstructure characteristics of the sample material.

27. An optical scatterometry process as in claim 26 wherein the incident light beam is transmitted at one or more selected angles of incidence with respect to an axis of the screen.

28. An optical scatterometry process as in claim 26 wherein:

the incident light beam is transmitted simultaneously at a plurality of selected angles of incidence with respect to an axis of the screen; and the incident light beam is transmitted simultaneously at a plurality of selected wavelengths.

29. An optical scatterometry process as in claim 26 wherein:

the incident light beam is transmitted sequentially at a plurality of selected angles of incidence with respect to an axis of the screen; and the incident light beam is transmitted sequentially at a plurality of selected wavelengths.

30. An optical scatterometer system comprising:

a sample material having periodic and diffractive microstructure characteristics to be analyzed;

light source means for transmitting an incident light beam to illuminate a point on the sample material;

screen means positioned between said sample material and said light source means to receive and display a pattern representative of light specularly reflected from said sample material and light scattered from said sample material, said screen means being constructed of a material that permits the pattern displayed thereon to be viewed from a side of the screen means opposite said sample material, said screen means including an aperture therein through which said incident light beam is directed to illuminate said point on said sample material;

camera means positioned on the same side of said screen means as said light source means to record the pattern displayed on said screen means; and microprocessor means coupled to said camera means for processing electrical signals received therefrom to provide a two-dimensional intensity distribution of the pattern recorded by said camera means, said two-dimensional intensity distribution being indicative of the periodic and diffractive microstructure characteristics of said sample material.

* * * * *